United States Patent
Sherman

(10) Patent No.: US 8,187,213 B2
(45) Date of Patent: *May 29, 2012

(54) APPARATUS, SYSTEM, AND METHOD FOR TRANSCUTANEOUSLY TRANSFERRING ENERGY

(75) Inventor: Jason T. Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/788,690

(22) Filed: May 27, 2010

(65) Prior Publication Data
US 2010/0241040 A1    Sep. 23, 2010

Related U.S. Application Data

(62) Division of application No. 11/172,316, filed on Jun. 30, 2005, now Pat. No. 7,780,613.

(51) Int. Cl.
*A61F 5/00*    (2006.01)
(52) U.S. Cl. ............................................ 602/23; 602/26
(58) Field of Classification Search ............ 601/3, 5, 601/51, 61; 602/23, 26, 20; 128/882; 607/3
See application file for complete search history.

(56) References Cited

U.S. PATENT DOCUMENTS

| | | | |
|---|---|---|---|
| 4,352,960 A | 10/1982 | Dormer et al. | |
| 4,436,684 A | 3/1984 | White | |
| 4,467,809 A | 8/1984 | Brighton | |
| 4,549,547 A | 10/1985 | Brighton et al. | |
| 4,830,021 A | 5/1989 | Thornton | |
| 4,918,745 A | 4/1990 | Hutchison | |
| 4,936,862 A | 6/1990 | Walker | |
| 5,211,165 A | 5/1993 | Dumoulin et al. | |
| 5,300,120 A | 4/1994 | Knapp et al. | |
| 5,350,379 A | 9/1994 | Spievack | |
| 5,356,411 A | 10/1994 | Spievack | |
| 5,362,996 A | 11/1994 | Yizraeli | |
| 5,383,915 A | 1/1995 | Adams | |
| 5,448,489 A | 9/1995 | Reuben | |
| 5,488,952 A | 2/1996 | Schoolman | |
| 5,522,402 A | 6/1996 | Cooley | |
| 5,536,269 A | 7/1996 | Spievack | |

(Continued)

FOREIGN PATENT DOCUMENTS

EP    1 570 782 A2    3/2005

(Continued)

OTHER PUBLICATIONS

European Search Report for European Patent Application No. 06253132.2-1257, Aug. 7, 2007, 8 pgs.

(Continued)

*Primary Examiner* — Michael A. Brown
(74) *Attorney, Agent, or Firm* — Barnes & Thornburg LLP

(57) ABSTRACT

An apparatus for transcutaneously transferring an amount of energy to an implantable orthopaedic device includes a primary coil. The primary coil has a resonant frequency matched to a resonant frequency of a secondary coil, which may form part of the implantable orthopaedic device. The primary coil may have an aperture configured to receive a portion of a patient's body or may include a substantially "C"-shaped core. A power circuit may be coupled with the primary coil to provide power to the coil. The apparatus may also include a wireless receiver, a measuring device, and/or a display.

20 Claims, 14 Drawing Sheets

U.S. PATENT DOCUMENTS

| | | | |
|---|---|---|---|
| 5,610,996 A | 3/1997 | Eller | |
| 5,626,579 A | 5/1997 | Muschler et al. | |
| 5,662,111 A | 9/1997 | Cosman | |
| 5,704,939 A | 1/1998 | Justin | |
| 5,715,837 A | 2/1998 | Chen | |
| 5,741,215 A | 4/1998 | D'Urso | |
| 5,741,316 A | 4/1998 | Chen et al. | |
| 5,798,924 A | 8/1998 | Eufinger et al. | |
| 5,807,258 A | 9/1998 | Cimochowski et al. | |
| 5,832,488 A | 11/1998 | Eberhardt | |
| 5,855,609 A | 1/1999 | Knapp | |
| 5,961,553 A | 10/1999 | Coty et al. | |
| 6,002,859 A | 12/1999 | DiGioia et al. | |
| 6,034,296 A | 3/2000 | Elvin et al. | |
| 6,083,174 A | 7/2000 | Brehmeier-Flick et al. | |
| 6,115,636 A | 9/2000 | Ryan | |
| 6,126,690 A | 10/2000 | Ateshian et al. | |
| 6,144,385 A | 11/2000 | Girard | |
| 6,151,581 A | 11/2000 | Kraftson et al. | |
| 6,161,080 A | 12/2000 | Aouni-Ateshian et al. | |
| 6,177,034 B1 | 1/2001 | Ferrone | |
| 6,239,705 B1 | 5/2001 | Glen | |
| 6,254,639 B1 | 7/2001 | Peckitt | |
| 6,336,929 B1 | 1/2002 | Justin | |
| 6,366,799 B1 | 4/2002 | Acker et al. | |
| 6,369,694 B1 | 4/2002 | Mejia | |
| 6,400,272 B1 | 6/2002 | Holtzman | |
| 6,442,432 B2 | 8/2002 | Lee | |
| 6,447,448 B1 | 9/2002 | Ishikawa et al. | |
| 6,458,161 B1 | 10/2002 | Gibbs et al. | |
| 6,459,943 B1 | 10/2002 | Suetani et al. | |
| 6,474,599 B1 | 11/2002 | Stomski | |
| 6,480,745 B2 | 11/2002 | Nelson et al. | |
| 6,529,127 B2 | 3/2003 | Townsend et al. | |
| 6,559,620 B2 | 5/2003 | Zhou et al. | |
| 6,565,576 B1 | 5/2003 | Stauch et al. | |
| 6,574,511 B2 | 6/2003 | Lee | |
| 6,656,135 B2 | 12/2003 | Zogbi et al. | |
| 6,674,883 B1 | 1/2004 | Wei et al. | |
| 6,687,131 B1 | 2/2004 | Miehling | |
| 6,700,547 B2 | 3/2004 | Mejia et al. | |
| 6,720,930 B2 | 4/2004 | Johnson et al. | |
| 6,750,866 B1 | 6/2004 | Anderson, III | |
| 6,772,002 B2 | 8/2004 | Schmidt et al. | |
| 6,793,496 B2 | 9/2004 | Edic et al. | |
| 6,799,066 B2 | 9/2004 | Steines et al. | |
| 6,804,558 B2 | 10/2004 | Haller et al. | |
| 6,833,790 B2 | 12/2004 | Mejia et al. | |
| 6,847,892 B2 | 1/2005 | Zhou et al. | |
| 6,947,004 B2 | 9/2005 | Mejia et al. | |
| 7,015,826 B1 | 3/2006 | Chan et al. | |
| 7,191,007 B2 | 3/2007 | Desai | |
| 7,191,013 B1 | 3/2007 | Miranda et al. | |
| 7,218,232 B2 | 5/2007 | DiSilvestro et al. | |
| 7,599,743 B2 | 10/2009 | Hassler, Jr. et al. | |
| 7,599,744 B2 | 10/2009 | Giordano et al. | |
| 2001/0051787 A1 | 12/2001 | Haller et al. | |
| 2002/0024450 A1 | 2/2002 | Townsend | |
| 2002/0065539 A1 | 5/2002 | Von Arx et al. | |
| 2002/0077562 A1 | 6/2002 | Kalgren et al. | |
| 2002/0128872 A1 | 9/2002 | Giammattei | |
| 2002/0135336 A1 | 9/2002 | Zhou et al. | |
| 2002/0151770 A1 | 10/2002 | Noll et al. | |
| 2002/0198740 A1 | 12/2002 | Roman | |
| 2003/0045787 A1 | 3/2003 | Schulze | |
| 2003/0067736 A1 | 4/2003 | Vahamaki et al. | |
| 2003/0069644 A1 | 4/2003 | Kovacevic | |
| 2003/0154411 A1 | 8/2003 | Hovik | |
| 2004/0008123 A1 | 1/2004 | Carrender | |
| 2004/0011137 A1 | 1/2004 | Hnat et al. | |
| 2004/0019384 A1 | 1/2004 | Kirking et al. | |
| 2004/0030395 A1 | 2/2004 | Blunn et al. | |
| 2004/0078219 A1 | 4/2004 | Kaylor et al. | |
| 2004/0113790 A1 | 6/2004 | Hamel et al. | |
| 2004/0138663 A1 | 7/2004 | Kosashvili et al. | |
| 2004/0138925 A1 | 7/2004 | Zheng | |
| 2004/0171924 A1 | 9/2004 | Mire et al. | |
| 2004/0178955 A1 | 9/2004 | Menache et al. | |
| 2004/0230226 A1* | 11/2004 | Bingham et al. | 607/3 |
| 2005/0010299 A1 | 1/2005 | Disilvestro | |
| 2005/0010300 A1 | 1/2005 | Disilvestro et al. | |
| 2005/0027330 A1 | 2/2005 | Govari | |
| 2005/0055316 A1 | 3/2005 | Williams | |
| 2005/0065815 A1 | 3/2005 | Mazar | |
| 2005/0075697 A1 | 4/2005 | Olson et al. | |
| 2005/0091338 A1 | 4/2005 | de la Huerga | |
| 2005/0099290 A1 | 5/2005 | Govari | |
| 2005/0101962 A1 | 5/2005 | Schwenke | |
| 2005/0113887 A1 | 5/2005 | Bauhahn et al. | |
| 2005/0119716 A1 | 6/2005 | McClure et al. | |
| 2005/0165317 A1 | 7/2005 | Turner et al. | |
| 2005/0288739 A1 | 12/2005 | Hassler | |
| 2005/0288740 A1 | 12/2005 | Hassler | |
| 2005/0288741 A1 | 12/2005 | Hassler, Jr. et al. | |
| 2006/0009856 A1 | 1/2006 | Sherman | |
| 2006/0030945 A1 | 2/2006 | Wright | |
| 2006/0074319 A1 | 4/2006 | Barnes et al. | |
| 2006/0136013 A1 | 6/2006 | Sherman | |
| 2006/0190080 A1 | 8/2006 | Danoff | |
| 2007/0005141 A1 | 1/2007 | Sherman | |
| 2007/0179627 A1 | 8/2007 | Gustilo et al. | |
| 2007/0239282 A1 | 10/2007 | Caylor et al. | |
| 2008/0065225 A1 | 3/2008 | Wasielewski et al. | |

FOREIGN PATENT DOCUMENTS

| | | |
|---|---|---|
| EP | 1 571 581 A1 | 3/2005 |
| EP | 1 611 835 A2 | 6/2005 |
| EP | 1 671 577 A1 | 12/2005 |
| EP | 1671577 A1 | 6/2006 |
| GB | 2239802 | 7/1991 |
| GB | 2 382 777 A | 6/2003 |
| WO | 9625117 | 8/1996 |
| WO | 9956614 | 11/1999 |
| WO | 00/13585 A1 | 3/2000 |
| WO | 0137926 | 5/2001 |
| WO | 01/49173 A1 | 7/2001 |
| WO | 0280753 | 10/2002 |
| WO | 02091399 | 11/2002 |
| WO | 02094113 | 11/2002 |
| WO | 2004026399 | 4/2004 |
| WO | 2005/084544 A1 | 9/2005 |
| WO | 2005/120203 A2 | 12/2005 |

OTHER PUBLICATIONS

European Search Report for European Patent Application No. 06253137.1-1526, Nov. 24, 2006, 9 pgs.

D'Lima et al., 2005, "An implantable telemetry device to measure intra-articulartibial forces", Journal of Biomechanics, 38 pp. 299-304 (6 pages).

Graichen et al., 1999, "Implantable Telemetry System for Measurement of Hip Joint Force and Temperature", 15th Int. Symposium of Biotelemetry, Juneau, Alaska, US (Abstract).

Want, Roy, "RFID a Key to Automating Everything", Scientific American, Jan. 2004, pp. 56-65 (13 pages).

European Office Action, European Patent Application No. 06253132.2-1257, May 6, 2011, 6 pages.

Friedmar Graichen et al., Hip Endoprosthesis for in Vivo Measurement of Joint Force and Temperature Original Research Article, Journal of Biomechanics, Pergamon Press, NewYork, vol. 32 No. 10, 1999, pp. 1113-1117.

* cited by examiner

APPARATUS, SYSTEM, AND METHOD FOR TRANSCUTANEOUSLY TRANSFERRING ENERGY

This application is a divisional of U.S. patent application Ser. No. 11/172,316, filed on Jun. 30, 2005. That application is incorporated in its entirety herein by reference.

CROSS-REFERENCE TO RELATED U.S. PATENT APPLICATION

Cross-reference is made to U.S. Utility patent application Ser. No. 11/171,869 entitled "Apparatus, System, and Method for Transcutaneously Transferring Energy" which was filed Jun. 30, 2005 by Jason T. Sherman, the entirety of which is expressly incorporated herein by reference. Cross-reference is made to U.S. Utility patent application Ser. No. 12/788,655 entitled "APPARATUS, SYSTEM, AND METHOD FOR TRANSCUTANEOUSLY TRANSFERRING ENERGY," which was filed on May 27, 2010 by Jason T. Sherman (265280-209270), the entirety of which is expressly incorporated herein by reference.

TECHNICAL FIELD

The present disclosure relates generally to transcutaneous energy transfer devices and methods, and more particularly to devices and methods for transcutaneously transferring energy to an implantable medical device.

BACKGROUND

Transcutaneous energy transfer (TET) devices are used to transfer energy across a boundary such as skin and other tissue of a patient. For example, a TET device may be used to transfer energy from a source external to a patient's body to a device implanted in the patient's body to power and/or recharge the device. Because the implanted device receives power transcutaneously, the implanted device typically does not require an implanted power source, such as a battery, to operate. As such, the patient is relieved from continual surgical operations to replace and/or recharge the implanted battery or other power sources.

SUMMARY

According to one aspect, an apparatus for transcutaneously transferring an amount of energy to an implantable orthopaedic device is disclosed. The apparatus may include a primary coil. The primary coil may have an aperture configured to receive a portion of a patient's body such as a leg, an arm, or the torso of the patient. The aperture may have, for example, an inner diameter of six inches or greater. Alternatively, the primary coil may be wound around a portion of a substantially "C"-shaped core. The "C"-shaped core may be, for example, a ferrite core. The core may include an elongated middle portion, which may be sized based on a length of the secondary coil of the implantable orthopaedic device. The core may also include two end portions extending substantially orthogonally from opposite distal ends of the elongated middle portion. In some embodiments, the primary coil may be coupled with a limb brace such as a leg or knee brace.

The primary coil may have a resonant frequency matched to a resonant frequency of a secondary coil of the implantable orthopaedic device. The resonant frequencies may be matched by use of a capacitive device such as a capacitor. In some embodiments, the resonant frequency of the primary coil is adjustable to match the resonant frequency of additional secondary coils.

The implantable orthopaedic device may include an electrical circuit configured to receive power from the secondary coil. For example, the electrical circuit may include a transmitter configured to transmit data in response to a power signal received from the secondary coil.

The apparatus may further include a power circuit which may supply a power signal to the primary coil to generate an alternating magnetic field. The power circuit may include a wireless receiver configured to receive data signals from the implantable orthopaedic device, a measuring device configured to measure an amount of power used by the primary coil, and/or a display configured to display the amount of power to a caregiver or user of the apparatus. In some embodiments, the power circuit includes a direct current power source and a converter configured to convert the direct current power source to an alternative current power signal. In such embodiments, the primary coil and the power circuit may be included in a portable housing.

According to another aspect, a method for determining a location of an orthopaedic device implanted in a patient's body is disclosed. The method may include moving or sweeping a primary coil over the patient's body or portion thereof. The amount of power used by the primary coil may be measured while the primary coil is being moved. The location may then be determined based on the amount of power used by the primary coil. That is, the location of the implanted orthopaedic device may be determined based on when the amount of power used by the primary coil is at or above a predetermined threshold value (e.g., a user defined maximum value). The method may further include tuning a resonant frequency of the primary coil to match a resonant frequency of a secondary coil of the implanted orthopaedic device. The method may also include receiving a wireless data signal from the implanted orthopaedic device.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

Figure 1:
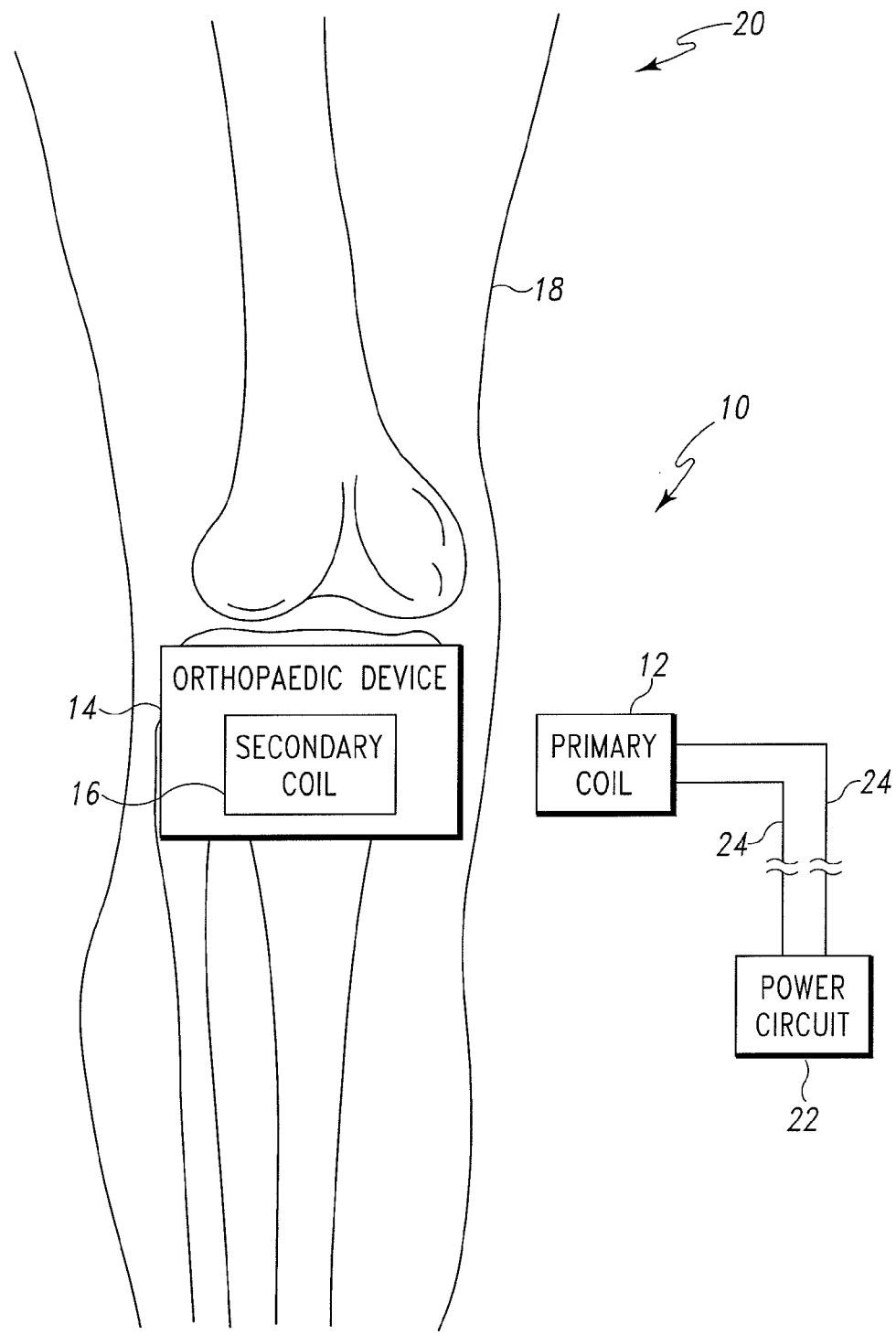
FIG. 1 is a diagrammatic view of a transcutaneous energy transfer system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a system 10 for transcutaneously transferring an amount of energy includes a primary coil 12 and an implantable orthopaedic device 14. The implantable orthopaedic device 14 includes a secondary coil 16. Illustratively, the orthopaedic device 14 is implanted in a leg 18 of a patient 20. However, in other embodiments, the device 14 may be implanted in any location of the patient 20. As such, the device 14 may be any type of implantable orthopaedic device such as, for example, a tibial tray implant, a bone distractor, or the like. Based on the particular application, the device 14 may include other electronic circuitry and/or devices such as sensors, processors, transmitters, electrical motors, actuators, or the like.

The primary coil 12 is coupled with a power circuit 22 via a number of interconnects 24. The power circuit 22 provides an alternating current power signal to the primary coil 12 to energize the primary coil 12. In response to the power signal, the primary coil 12 generates an alternating magnetic field. While the primary coil 12 is positioned near the implanted orthopaedic device 14 such that the primary coil 12 and the secondary coil 16 are inductively coupled, the alternating magnetic field generated by the primary coil 12 induces a current in the secondary coil 16. In this way, energy is transferred from the primary coil 12 to the secondary coil 16. It should be appreciated that the primary coil 12 may be positioned such that the coil 12 inductively couples with the secondary coil 16 while not coming into contact with the skin of the patient 20.

To improve the efficiency of the energy transfer between the coils 12, 16, the resonant frequency of the primary coil 12 is matched to the resonant frequency of the secondary coil 16 of the orthopaedic device 14. As used herein in reference to resonant frequencies, the terms "match", "matched", and "matches" are intended to mean that the resonant frequencies are the same as or within a predetermined tolerance range of each other. For example, the resonant frequency of the primary coil 12 would match the resonant frequency of the secondary coil if the current induced in the secondary coil 16 is sufficient to power an electrical circuit or device coupled therewith. Conversely, the resonant frequencies of the coils 12, 16 would not match if the current induced in the secondary coil 16 is insufficient to power the electrical circuit or device. The resonant frequency of the primary coil 12 and the secondary coil 16 may be configured using a capacitive device, such as a capacitor, as discussed in more detail below in regard to FIGS. 11 and 12. The resonant frequency of the primary coil 12 and the secondary coil 16 may be matched to any frequency. However, in some embodiments, the resonant frequency of the coils 12, 16 is configured to a frequency such that patient exposure to magnetic fields is reduced. For example, in some embodiments the resonant frequencies of the coils 12, 16 are matched to a resonant frequency of about 9 kilohertz or lower. In one particular embodiment, the resonant frequencies of the coils 12, 16 are matched to a resonant frequency of about 5 kilohertz. The frequency of the power signal produced by the power circuit 22 is also matched to the resonant frequency of the primary coil 12. In some embodiments, the resonant frequency of the primary coil 12 and the power circuit 22 may be adjustable to match the resonant frequencies of other secondary coils of other implantable orthopaedic devices. In this way, different orthopaedic devices (i.e. the secondary coils of the orthopaedic devices) may have different resonant frequencies to allow selective energy transfer to one implanted orthopaedic device while reducing the amount of energy inadvertently transferred to other implanted orthopaedic devices (i.e., the resonant frequencies of the other implanted orthopaedic devices do not match the resonant frequency of the primary coil 12). The resonant frequency of the primary coil may, however, be adjusted to match the resonant frequency of the other implantable devices to transfer energy to such devices.

Figure 2:
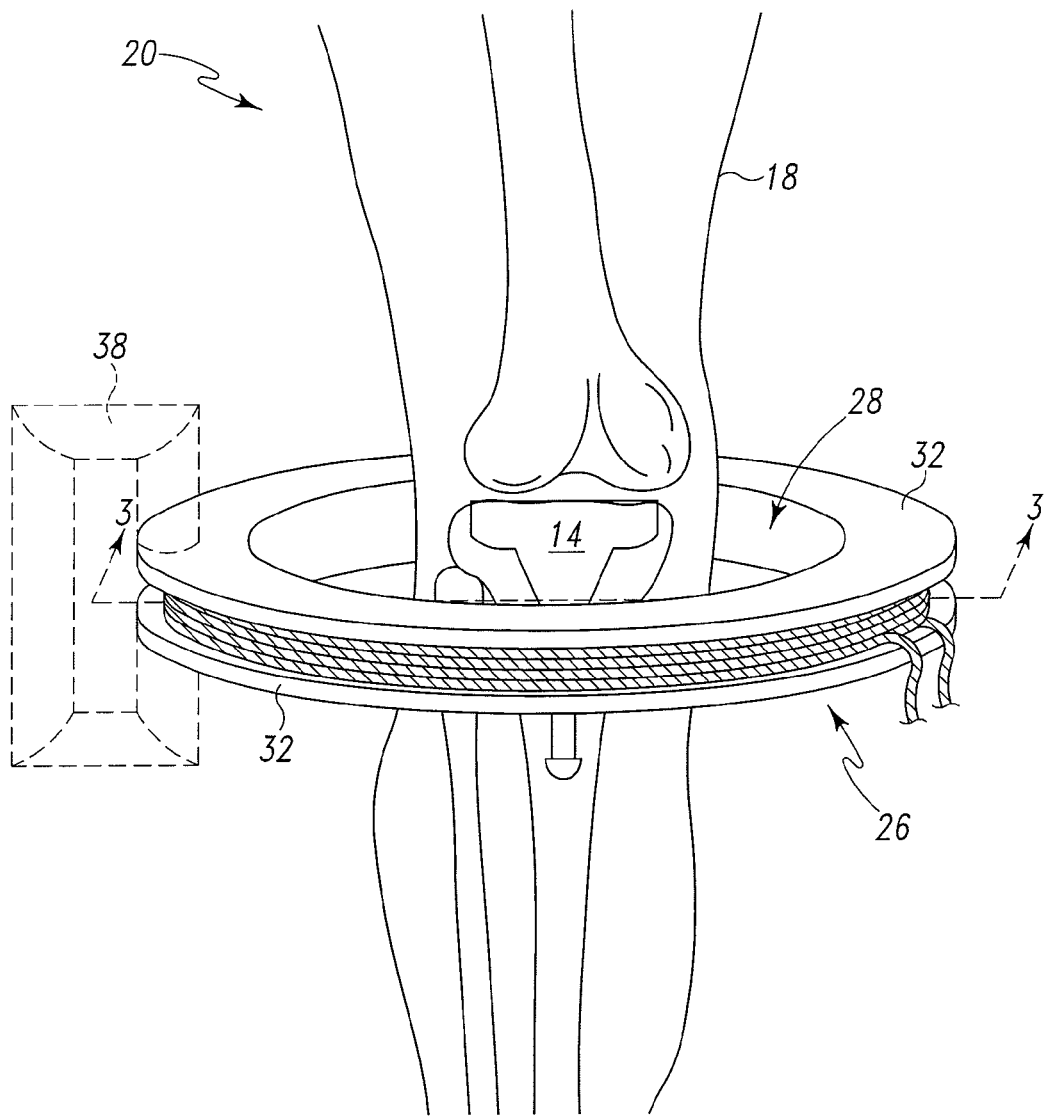
FIG. 2 is a perspective view of one embodiment of the primary coil of the transcutaneous energy transfer system of FIG. 1.
Figure 3:
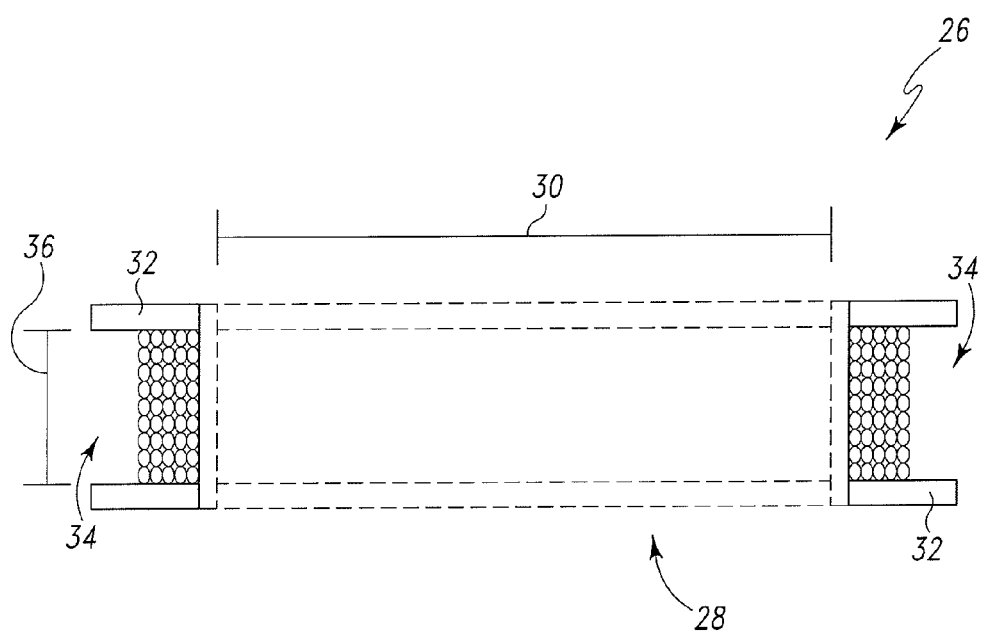
FIG. 3 is a cross-sectional view taken generally along section lines 3-3 of FIG. 2 (note the patient's limb is not shown for clarity of description)

Referring now to FIG. 2, in one embodiment, the primary coil 12 is embodied as a primary coil 26 having an aperture 28 configured to receive a portion of the patient's 20 body. Illustratively, the aperture 28 is configured to receive a leg 18 of the patient 20. However, in other embodiments, the aperture 28 may be configured to receive any portion of the patient's 20 body including, for example, an arm, a finger, the head, or the torso of the patient 20. That is, the primary coil 12 has an inner diameter 30, as illustrated in FIG. 3, of sufficient length to allow the portion of the patient's 20 body to be received by the aperture 28 while allowing the primary coil 26 to be spaced away from the skin of the patient 20 (i.e., an air gap is present between the primary coil 26 and the skin of the patient 20). In one embodiment, the aperture 28 of the primary coil 26 may have an inner diameter 30 greater than about six inches. In one particular embodiment, the aperture 28 has an inner diameter 30 of about 8.5 inches.

Illustratively, the primary coil 26 is toroidal in shape, but primary coils having other shapes capable of including the aperture 28 may be used. For example, primary coils having square or rectangular shapes may be used. The primary coil 26 is wound around a bobbin 32 as illustrated in FIG. 2. The bobbin 32 may be formed from any nonmagnetic and non-conductive material such as, for example, a plastic material. The bobbin 32 provides a support structure for the primary coil 26 and may, similar the primary coil 26, have a toroidal shape or other shape capable of defining an aperture configured to receive a portion of the patient 20. The primary coil 26 is formed from individual turns. The number of turns which form the primary coil 26 may vary depending upon the particular application and required magnetic intensity. The individual turns are wound around the bobbin 32 and positioned in a coil track 34. The coil track 34 has a height 36 configured to accommodate the number of turns. That is, the height 36 may be increased to accommodate additional individual turns. In one particular embodiment, the height 36 of the coil track 34 has a track height 34 of about 1.5 inches. To improve conductivity (i.e., reduce the effects of the "skin effect") of the primary coil 26 at operating frequencies, the coil 26 may be formed from Litz wire (i.e., wire formed from a number of individual strands of wire). Depending on the desired resonant frequency of the primary coil 26, the Litz wire may have a strand count greater than about fifty strands. In one particular application, the primary coil 26 is formed from Litz wire having a strand count of about 100 strands. In addition, in some embodiments, the primary coil 26 may be formed from a number of individual, parallel coils to reduce the voltage requirements of each individual coil.

In use, a portion of the patient 20, such as the leg 18, is positioned in the aperture 28 of the primary coil 26. The primary coil 26 is positioned such that the coil 26 is substantially coplanar with the orthopaedic device 14 and circumferentially surrounds the portion of the patient 20. For example, the primary coil 26 may be positioned such that the coil 26 and the secondary coil 16 of the device 14 may be inductively coupled. To do so, a caregiver (e.g., a physician, a nurse, or the like) may grasp a portion of the bobbin 32 to move the primary coil 26 to the desired location. In some embodiments, a handle 38 may be coupled with a portion of the bobbin 32 to facilitate the positioning of the primary coil 26. Once the primary coil 26 is located in the desired position, an alternating current power signal may be applied to the primary coil 26. In response to the power signal, the primary coil 26 generates an alternating magnetic field. The power signal and primary coil 26 are configured such that the alternating magnetic field generated by the coil 26 extends into the portion (e.g., the leg 18) of the patient 20. The magnetic field is received by the secondary coil 16 of the orthopaedic device 14. As discussed above, the alternating magnetic field produces a current in the secondary coil 26 which may be used to power electrical circuitry and/or devices coupled with the coil 26.

Figure 4:
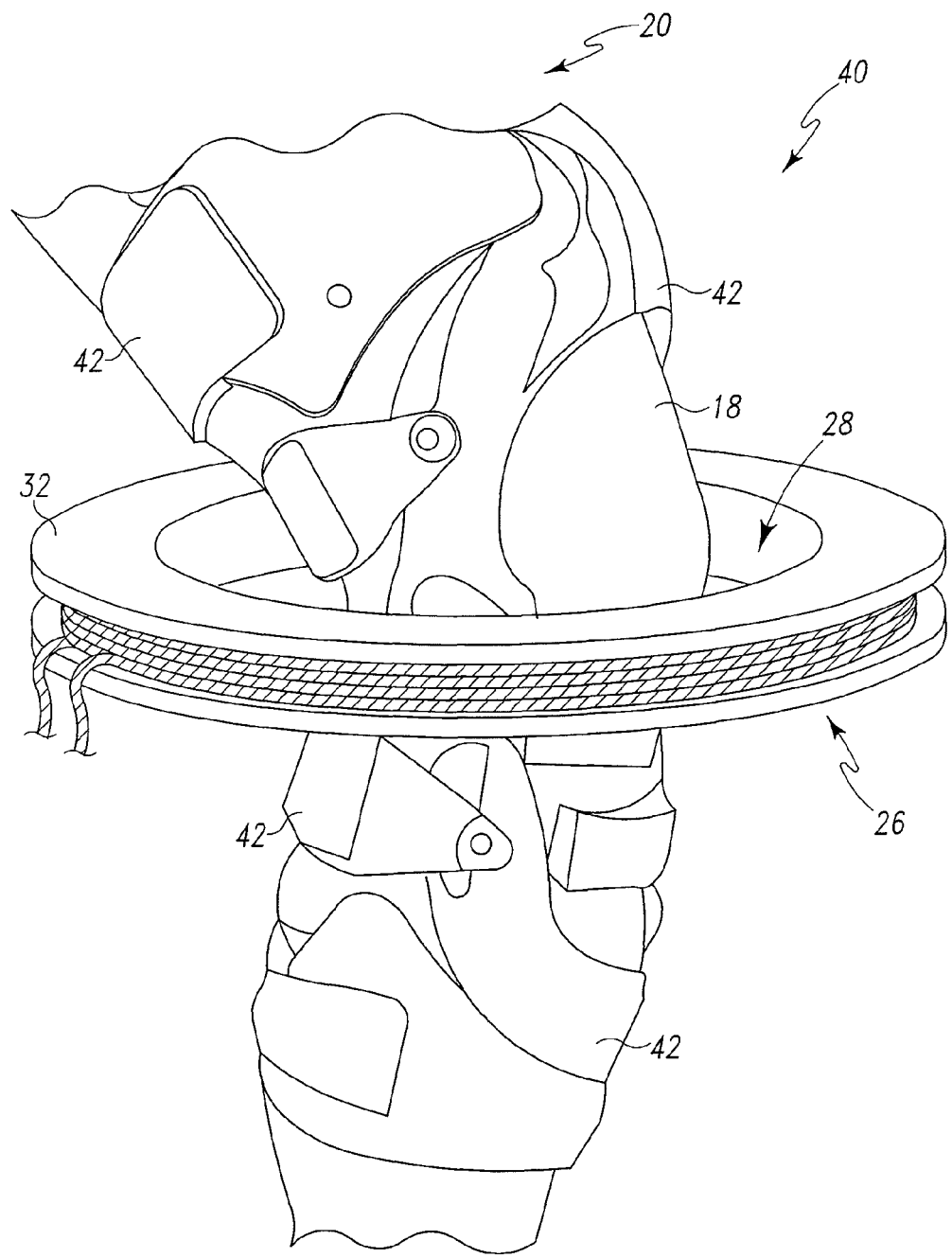
FIG. 4 is a perspective view of a leg brace having the primary coil of FIG. 2 coupled therewith.

Referring now to FIG. 4, in some embodiments, the primary coil 26 may be included in a limb brace 40 to provide better stability for the coil 26 during operation of the system 10. The limb brace 40 may be any type of limb brace configured to couple to any limb of the patient 20. Illustratively, the limb brace 40 is a leg brace, commonly referred to as a knee brace, configured to couple to the leg 18 of the patient 20. The limb brace 40 includes a brace structure 42. The brace structure 42 includes coupling means, such as straps, snaps, hook and loop fasteners, or the like, to secure the structure 42 to the leg 18 or other limb of the patient 20. The primary coil 26 is coupled with the bracing structure 42 via, for example, mounting posts or the like. The primary coil 26 may be permanently mounted to the bracing structure 42 such that the primary coil 26 is positioned in a similar location every time the limb brace 40 is worn by the patient 20. Alternatively, the primary coil 26 may be movable about the bracing structure 42 to allow the coil 26 to transfer energy to implantable orthopaedic devices located in regions in addition to the knee area of the patient 20. Regardless, because the primary coil 26 is coupled with the limb brace 40, the caregiver is not required to constantly hold the primary coil 26 in the desired position. Additionally, the primary coil 26 may be used to transfer energy while the patient 20 is performing an exercise such as walking or jogging. In other embodiments, the primary coil 26 may be coupled with a stand or other structure to stabilize the primary coil 26 and allow the primary coil 26 to be inserted over the portion of the patient 20 without the aid of the caregiver.

Figure 5:
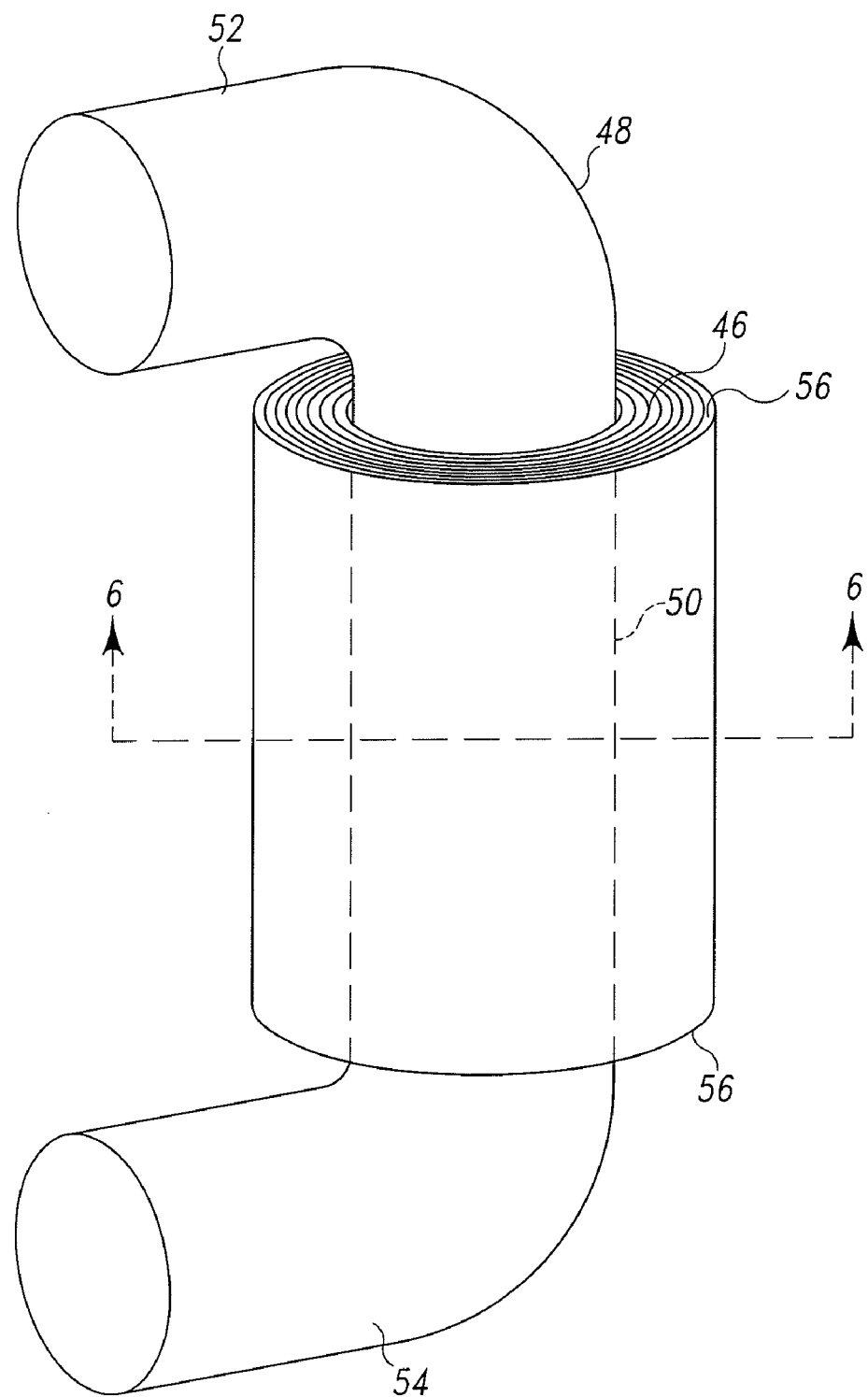
FIG. 5 is a perspective view of another embodiment of the primary coil of the transcutaneous energy transfer system of FIG. 1.
Figure 6:
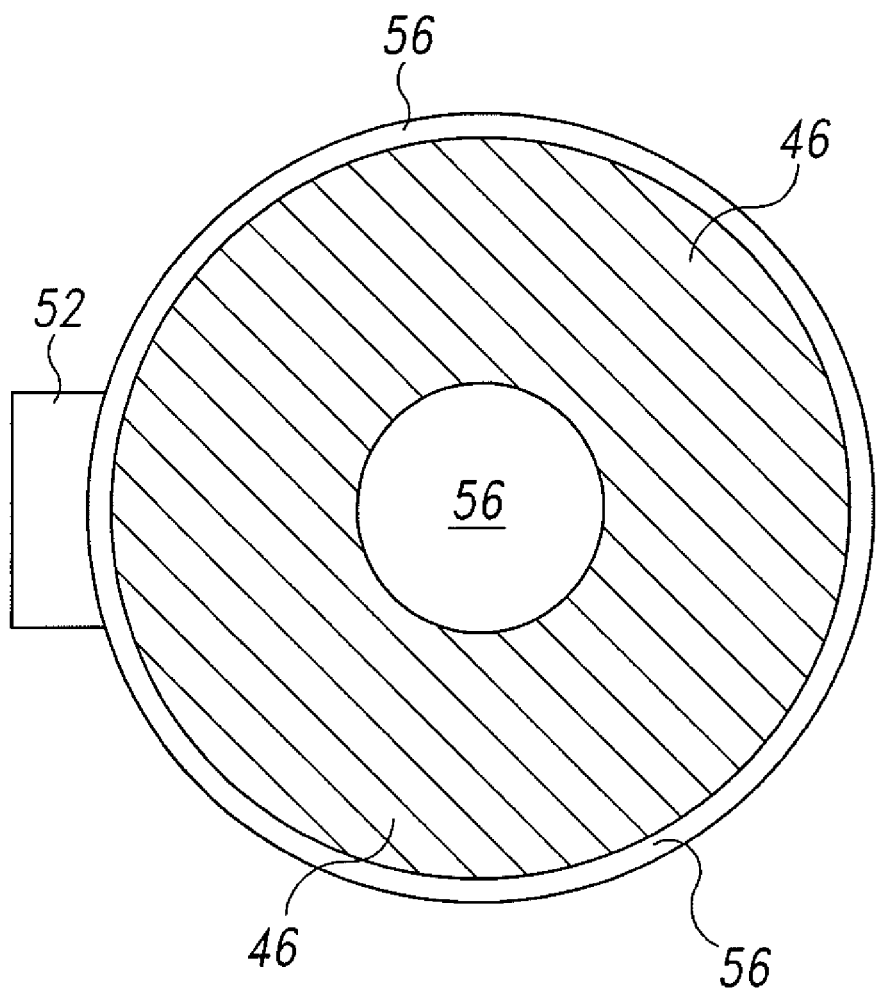
FIG. 6 is a cross-sectional view taken generally along section lines 6-6 of FIG. 5.

Referring now to FIGS. 5 and 6, in another embodiment, the primary coil 12 may be embodied as a primary coil 46 wound around a portion of a substantially "C"-shaped core 48. The core may be made from any ferrous material such as iron, ferrite, or the like. In the illustrative embodiment, the core 48 is formed from a unitary core having an elongated middle portion 50, a first end portion 52, and a second end portion 54. In some embodiments, the elongated middle portion 50 has a length based on the length of the secondary coil 16. The first and second end portions 52, 54 extend substantially orthogonally from the middle portion 50 at opposite distal ends and are coplanar with each other. However, in other embodiments, the substantially "C"-shaped core 48 may be formed from a middle portion and two end portions coupled with the middle portion using a suitable adhesive. Additionally, although the illustrative core 48 has a circular shaped cross-section, cores having other geometric cross sections, such as square or rectangular, may be used in other embodiments. Regardless, the "C"-shaped core 48 is configured such that the magnetic field generated by the primary coil 46 is increased in the direction of the end portions 52, 54. That is, the magnetic field extends further away from the primary coil 46 ins the direction of the end portions 52, 54.

Similar to the primary coil 26, the primary coil 46 is formed from individual turns, which may, in some embodiments, be formed from Litz wire. The individual turns which form the primary coil 46 are wound around the elongated middle portion 50 of the core 48. In some embodiments, an insulator film (not shown) is wrapped around the core 48 prior to the primary coil 46 being wound thereon to insulate the turns of the coil 46 from the core 48. Alternatively, in some embodiments, a bobbin (not shown) having an aperture configured to receive the core 48 is used. In such embodiments, the primary coil 46 is wound around the bobbin, which forms an insulative barrier between the coil 46 and the core 48. Additionally, in some embodiments, a sleeve 56 may be positioned around the outside of the primary coil 46 to protect the coil 46. The sleeve 56 may be formed from any nonmagnetic and nonconductive material such as plastic or the like.

Figure 7:
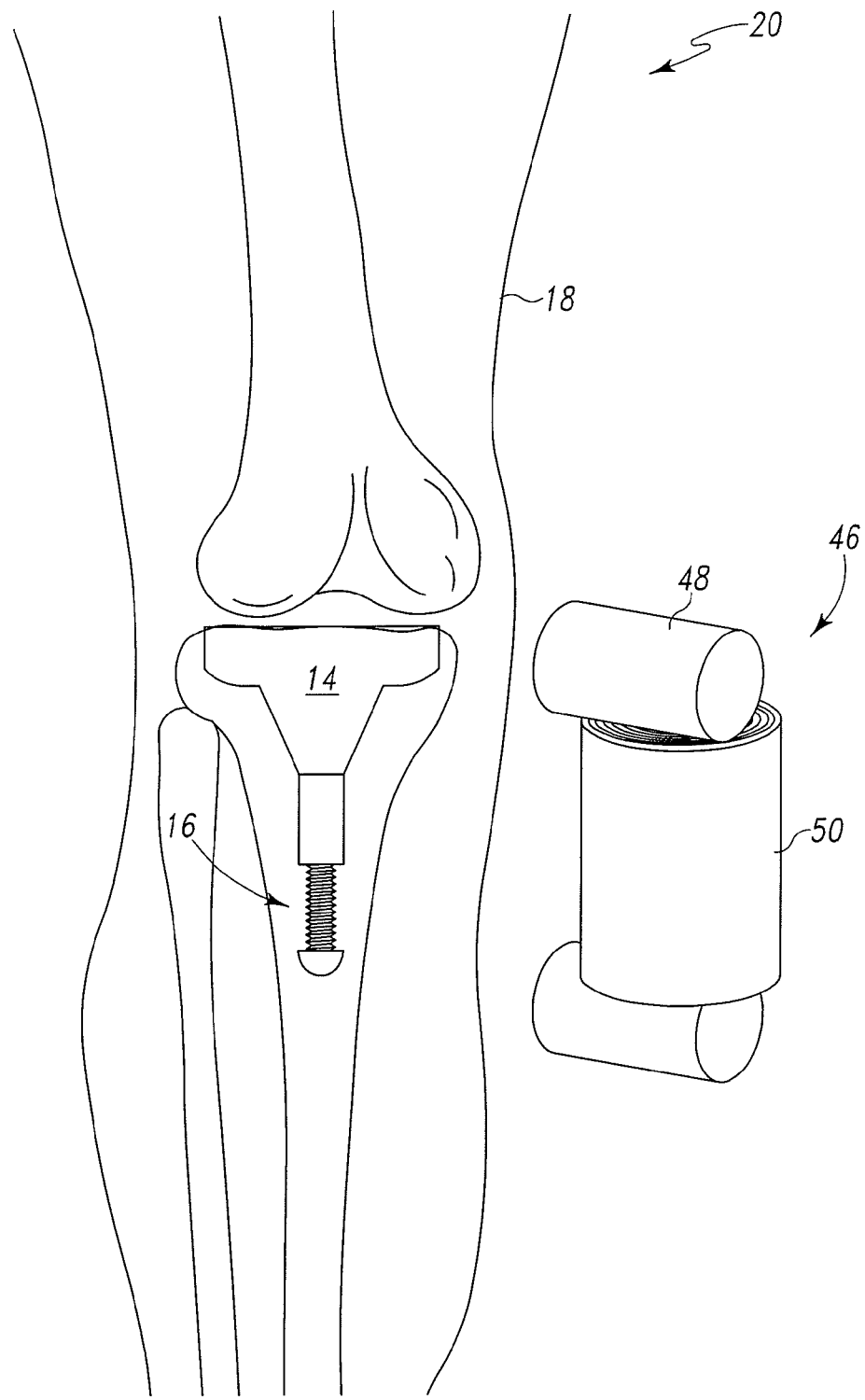
FIG. 7 is an elevational view showing the primary coil of FIG. 5 being used to transfer energy to an implanted orthopaedic device.

Referring now to FIG. 7, in use, the primary coil 46 is positioned near the portion of the patient's 20 body wherein the orthopaedic device 14 is implanted. The primary coil 46 is positioned such that the coil 46 is substantially coplanar with the implanted orthopaedic device 14. For example, the primary coil 46 may be positioned such that the coil 46 and the secondary coil 16 of the device 14 may be inductively coupled. To do so, a caregiver may grasp the sleeve 50 to move the primary coil 46 to the desired location. In some embodiments, the primary coil 46 and the core 48 are housed in a portable housing having a handle or the like to facilitate the positioning of the primary coil 46. Once the primary coil 26 is located in the desired position, an alternating current power signal may be applied to the primary coil 46. In response to the power signal, the primary coil 46 generates an alternating magnetic field. The power signal and primary coil 46 are configured such that the alternating magnetic field generated by the coil 26 extends into the leg 18 or other portion of the patient 20. The magnetic field is received by the secondary coil 16 of the implanted orthopaedic device 14. As discussed above in regard to FIG. 1, the alternating magnetic field produces a current in the secondary coil 26 which may be used to power electrical circuitry and/or devices coupled with the coil 26.

Figure 8:
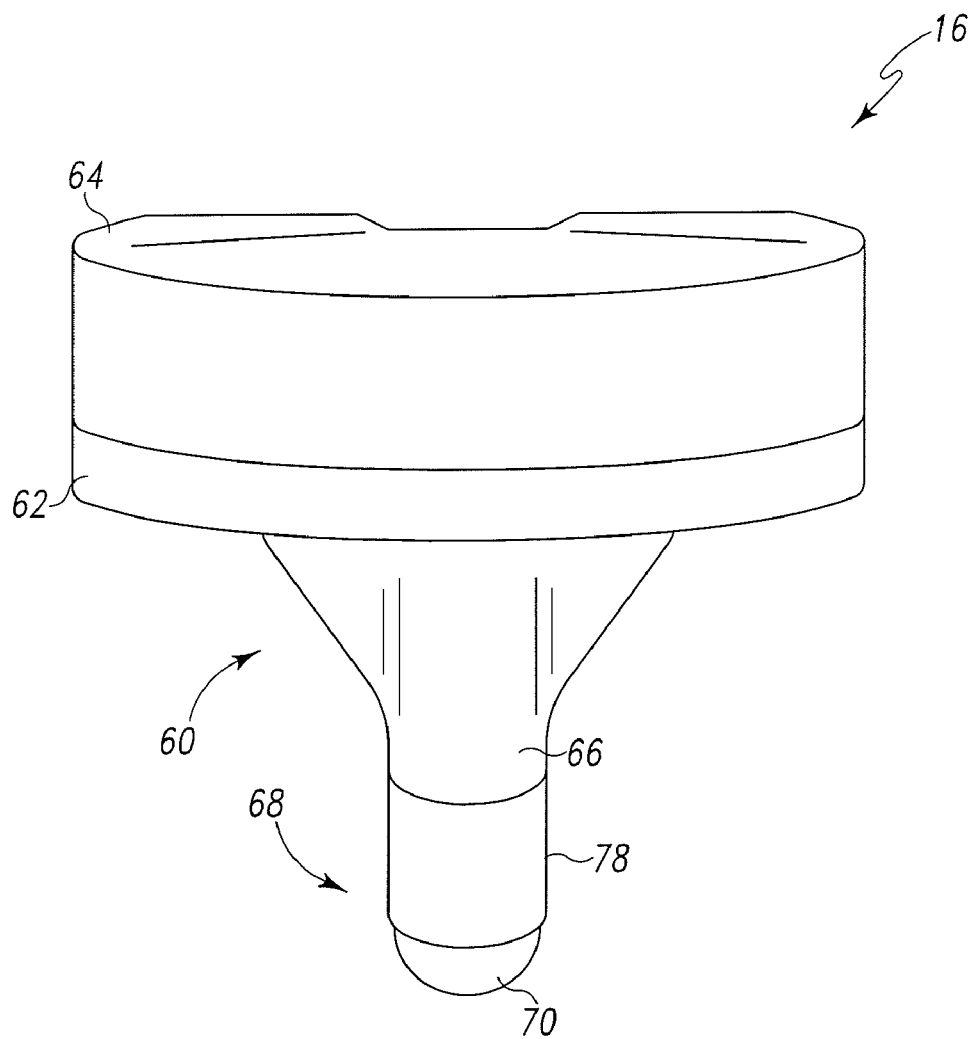
FIG. 8 is an elevational view of a tibial tray.
Figure 9:
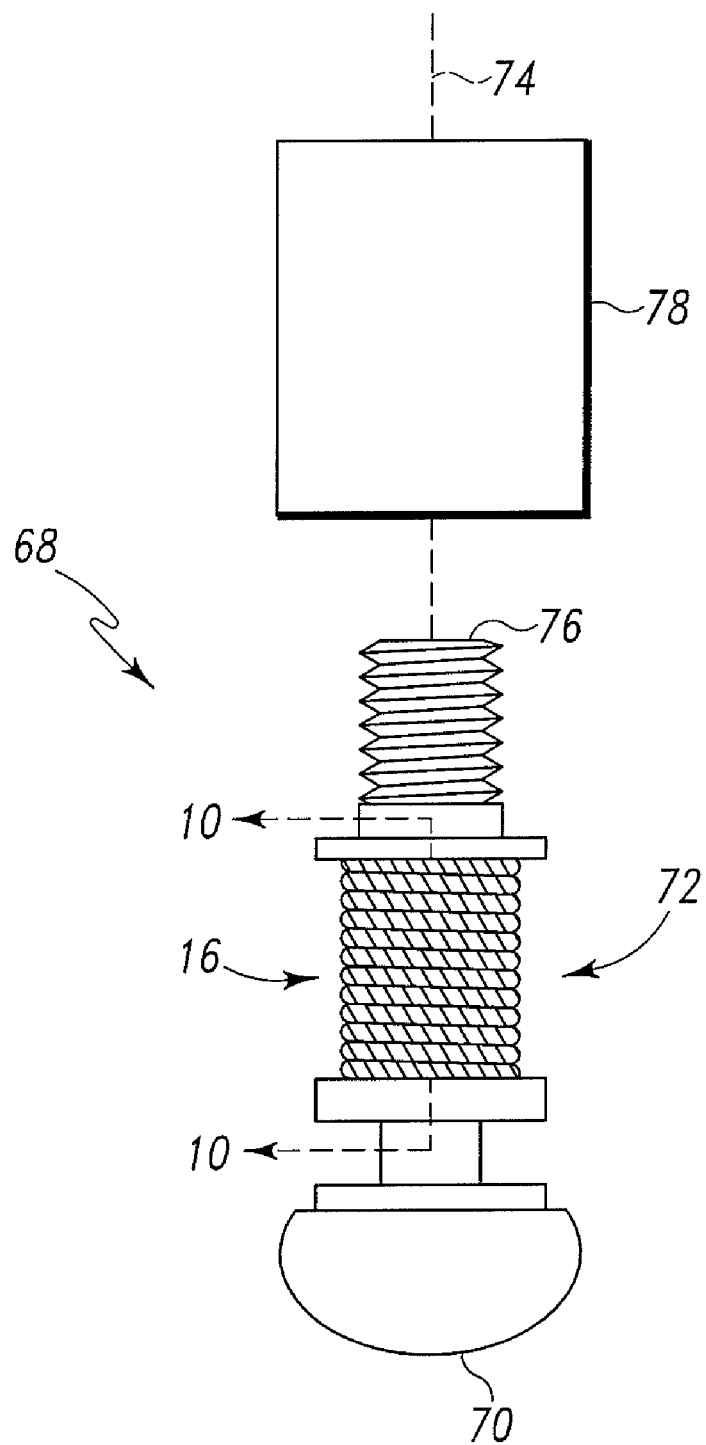
FIG. 9 is an exploded elevational view of the secondary coil and bobbin assembly of the tibial tray of FIG. 8.

Referring now to FIG. 8, in one embodiment, the implantable orthopaedic device 14 includes a tibial tray 60. The tibial tray 60 is configured to be coupled with a tibia of the patient 20 during a surgical procedure such as a total knee anthroplasty procedure. The tibial tray 60 includes a platform 62 for supporting a bearing insert 64. The insert 64 provides a bearing surface for a femur or femur implant to articulate. The tibial tray 60 also includes a stem portion 66 for securing the tray 60 to the tibia of the patient 60. The stem portion 66 is configured to be inserted into a resected end portion of the tibia and may be secured in place by use of bone cement, although cementless configurations may also be used. The tibial tray 60 also includes a bobbin assembly 68 secured to a distal end of the stem portion 66. As illustrated in FIG. 9, the bobbin assembly 68 includes a screw head 70 having a hemispherical shape and a bobbin 72 extending axially from the screw head 70 in the direction of an axis 74. The bobbin assembly 68 also includes a thread portion 76 that extends axially from the bobbin 72 in the direction of an axis 74. The bobbin assembly 68 may be formed from any nonmagnetic material such as a plastic material.

Figure 10:
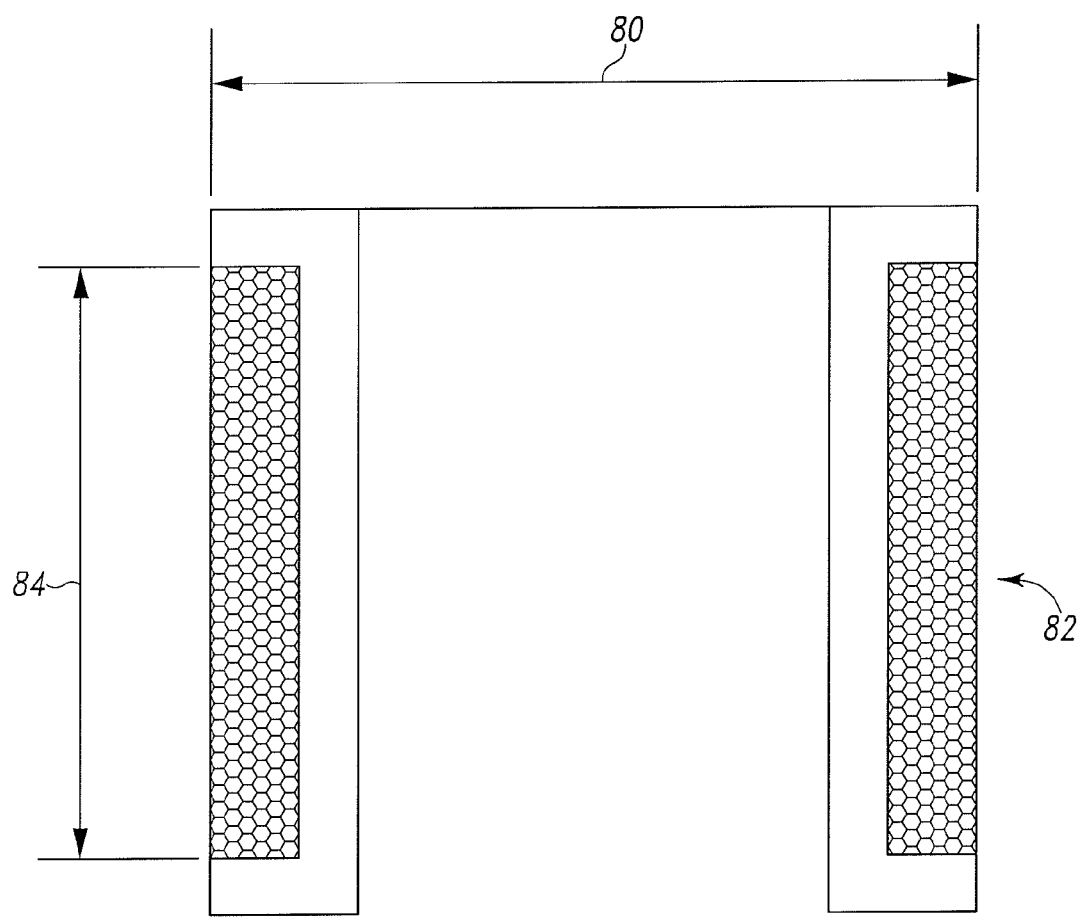
FIG. 10 is a cross-sectional view taken generally along the section lines 6-6 of FIG. 5.

The secondary coil 16 is wound around the bobbin 72 of the bobbin assembly 68. Illustratively, solid wire is used to form the primary coil 16, but in other embodiments, Litz wire may be used. Similar to the primary coil 12, the secondary coil 16 is formed from a number of individual turns. The individual turns of the secondary coil 16 are wound around the bobbin 72 in a coil track 82. The dimensions of the bobbin 72 are based upon the particular application and implantable orthopaedic device 14 being used. For example, as illustrated in FIG. 10, the bobbin 72 may have an outer diameter 80 and a coil track width 84 sized based on the number of individual turns of the secondary coil 16. That is, the outer diameter 80 and/or the coil track width 84 may be increased to accommodate additional individual turns. To protect the secondary coil 16, a sleeve 78 is configured to slide over the secondary coil 16 when the bobbin assembly 68 is secured to the stem portion 66 (via the thread portion 76). The sleeve 78 may also be formed from any type of nonmagnetic material such as a plastic or rubber material.

As discussed in more detail below in regard to FIG. 11, the implantable orthopaedic device 14 may also include additional electronic circuitry and/or devices. The secondary coil 16 provides power to such electronic circuitry and devices. In some embodiments, the additional electronic circuitry is coupled with the insert 64 (e.g., embedded in the insert 64). In other embodiments, the electronic circuitry may be coupled with the tibial tray 60. Regardless, wires or other interconnects from the secondary coil 16 may be routed up through the stem portion 66 of the tibial tray 60 and coupled with the electronic circuitry and/or devices.

Figure 11:
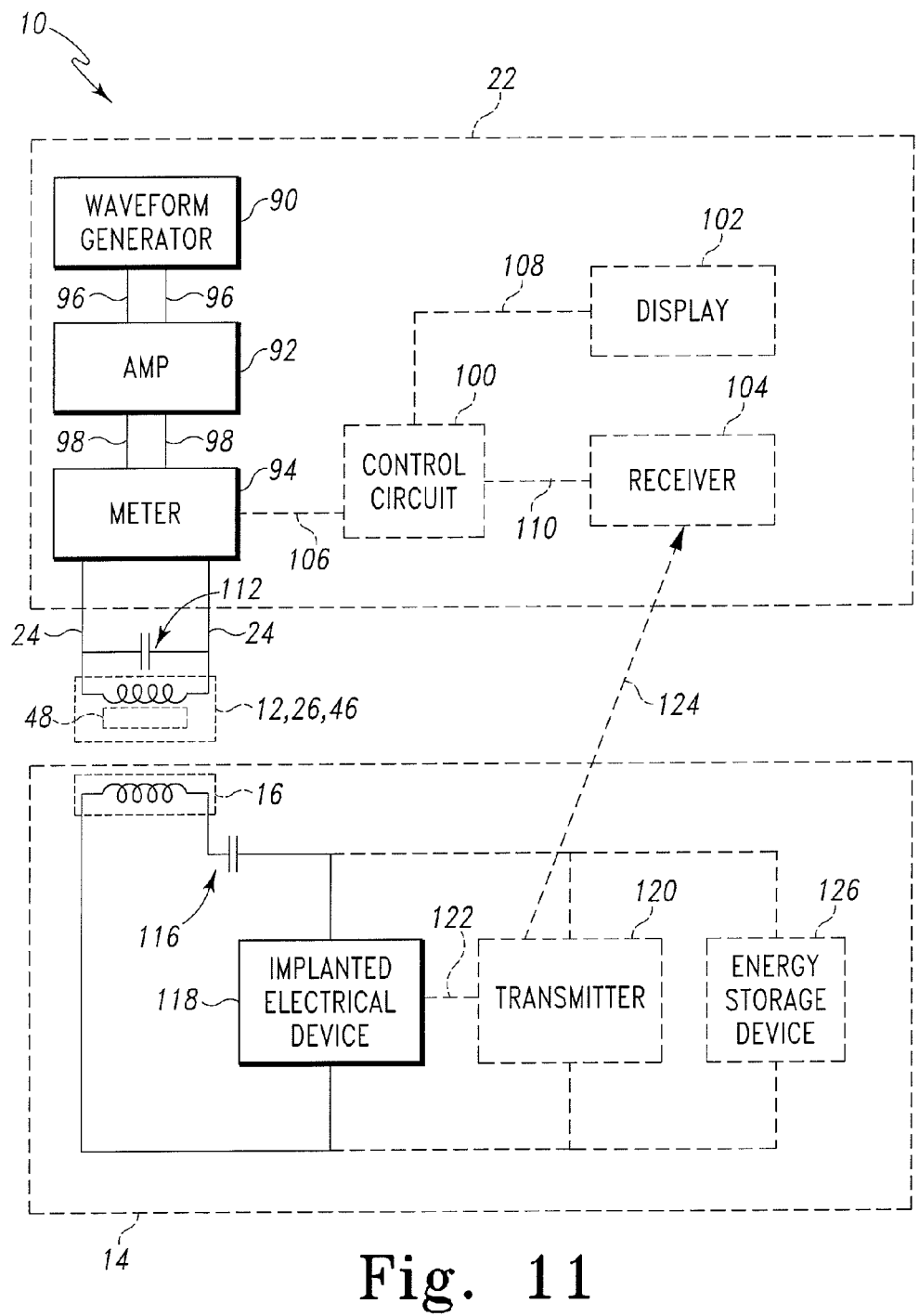
FIG. 11 is a block diagram of one embodiment of a transcutaneous energy transfer system.

Referring now to FIG. 11, in one embodiment, the power circuit 22 of the system 10 includes a waveform generator 90, an amplifier 92, and a meter 94. The waveform generator 90 is coupled with the amplifier 92 via a number of interconnects 96. The interconnects 96 may be embodied as any type of interconnects capable of providing electrical connection between the generator 90 and the amplifier 92 such as, for example, wires, cables, PCB traces, or the like. The waveform generator 90 may be any type of waveform generator that is capable of producing an output signal having a frequency that matches the resonant frequency of the primary coil 12, 26, 46. For example, the waveform generator 90 may be formed from discrete and/or integrated circuitry. Alternatively, the waveform generator 90 may be formed from a stand-alone waveform generation device. For example, in one embodiment, the waveform generator 90 is embodied as a PCI-5401 Single Channel Arbitrary Function Generator for PCI commercially available from National Instruments of Austin, Tex.

The amplifier 92 is configured to amplify the output signal received from the generator 90 and produce an amplified output signal having a predetermined amplitude. The predetermined amplitude of the amplified output signal may be determined based on the particular primary coil 12, 26, 46 used and/or the application of the system 10. For example, in embodiments including primary coil 26, an amplified output signal having a higher amplitude may be used due to the increased distance between the coil 26 and the secondary coil 16. Comparatively, in embodiments including primary coil 46, an amplified output signal having a lower amplitude may be used due to the increased inductive coupling efficiency provided by the core 48. The amplifier 92 may be any type of amplifier capable of amplifying the output signal of the waveform generator to the predetermined amplitude. For example, the amplifier 92 may be formed from discrete and/or integrated circuitry. Alternatively, the amplifier 92 may be formed from a stand-alone amplification device. For example, in one embodiment, the amplifier 92 is embodied as a model AR-700A1 Amplifier commercially available from Amplifier Research of Souderton, Pa.

The meter 94 is coupled with the amplifier 92 via a number of interconnects 98 and to the primary coil 12, 26, 46 via the interconnects 24. The interconnects 98 may be embodied as any type of interconnects capable of providing electrical connection between the meter 94 and the amplifier 92 such as, for example, wires, cables, PCB traces, or the like. The meter 94 is configured to measure the amount of power supplied to (i.e., used by) the primary coil 12, 26, 46. In some embodiments, the meter 94 is coupled in parallel with the outputs of the amplifier 94 (i.e., the amplifier 92 is coupled directly to the primary coil 12, 26, 46 and to the meter 94). In other embodiments, the meter 94 may have a pass-through input-output configuration. Regardless, the meter 94 has a large input impedance such that the effects of the meter 94 on the amplified power signal are reduced. The meter 94 may be any type of meter capable of measuring the power supplied to the primary coil 12, 26, 46. For example, the amplifier 92 may be formed from discrete and/or integrated circuitry. Alternatively, the amplifier 92 may be formed from a stand-alone amplification device. For example, in one embodiment, the meter 94 is embodied as Model 2330 Sampling Watt Meter commercially available from Clarke-Hess Communication Research Corporation of Long Island City, N.Y.

In some embodiments, the power circuit 22 may also include a control circuit 100, a display 102, and a receiver 104. The control circuit 100 may be communicatively coupled with the meter 94 via a number of interconnects 106, with the display 102 via a number of interconnects 108, and with the receiver 104 via a number of interconnects 110. The control circuit 100 may be embodied as any type of control circuit capable of performing the functions described herein including, but not limited to, discrete circuitry and/or integrated circuitry such as a processor, microcontroller, or an application specific integrated circuit (ASIC). The receiver 104 is configured to wirelessly receive data from the implantable orthopaedic device 14 and transmit the data to the control circuit 100. The control circuit 100 may display the data, or computed data based thereon, on the display 102. Additionally, the control circuit 100 may display power usage data received from the meter 94 on the display 102. The display 102 may be embodied as any type of display capable displaying data to the caregiver including, for example, a segmented light emitting diode (LED) display, a liquid crystal display (LCD), or the like.

The power circuit 22 is coupled with the primary coil 12, 26, 46 via the interconnects 24. In embodiments including the primary coil 46, the primary coil 46 includes the substantially "C"-shaped core 48. A tuning capacitor 112 is coupled in parallel with the primary coil 12, 26, 46 (i.e., the capacitor 112 and the primary coil 12, 26, 46 form a parallel resonance circuit). The tuning capacitor 112 is used to configure the resonant frequency of the primary coil 12, 26, 46. That is, the capacitance value of the tuning capacitor 112 is selected such that the resulting resonant frequency of the primary coil 12, 26, 46 matches the resonant frequency of the secondary coil 16. In addition, in some embodiments, the turning capacitor 112 is selected such that the quality factor (Q) of the resulting resonance curve is high. In such embodiments, the resonant frequency of the primary coil 12, 26, 46 matches a narrower bandwidth of frequencies.

In some embodiments, the tuning capacitor 112 is physically coupled to a portion (e.g., bobbin 32) of the primary coil 12, 26, 46 such that the tuning capacitor 112 moves with the primary coil 12, 26, 46. In other embodiments, the tuning capacitor 112 may be included in the power circuit 22. Alternatively, the tuning capacitor 112 may be separate from both the power circuit 22 and the primary coil 12, 26, 46. Additionally, in some embodiments, the tuning capacitor 112 is embodied as a capacitive device having a variable capacitance value. In such embodiments, the resonant frequency of the primary coil 12, 26, 46 may be adjusted to match the resonant frequency of other secondary coils by adjusting the capacitance value of the capacitor 112 and reconfiguring the resonant frequency of the power signal. The degree to which the resonant frequency of the primary coil 12, 26, 46 can be tuned is dependant up the granularity of the capacitance values obtainable with the variable capacitive device (i.e., the selection of available capacitance values). However, fine tuning of the resonant frequency may be accomplished by configuring the frequency of the power signal via the waveform generator 90. In one embodiment, the tuning capacitor 112 is embodied as a CS-301 Capacitance Substituter commercially available from IET Labs, Incorporated of Westbury, N.Y.

The implantable orthopaedic device 14 includes the secondary coil 16, a tuning capacitor 116 coupled in series with the secondary coil 16, and an implanted electrical device 118 coupled in parallel with the secondary coil 16 and the tuning capacitor 116. The capacitor 116 and the secondary coil 16 form a series resonance circuit. The tuning capacitor 116 is used to configure the resonant frequency of the secondary coil 116. That is, the capacitance value of the tuning capacitor 116 is selected such that the resulting resonant frequency of the secondary coil 16 is equal to a predetermined frequency. In addition, in some embodiments, the turning capacitor 116 is selected such that the quality factor (Q) of the resulting resonance curve is low. In such embodiments, the resonant frequency of the secondary coil 16 matches a broader bandwidth of frequencies.

The implanted electrical device 118 may be embodied as any electrical circuit(s), electrical device(s), or combination thereof, capable of being housed in or on the implantable orthopaedic device 14 and powered by the current produced by the secondary coil 16. For example, the implanted electrical device 118 may include, but is not limited to, sensors such as magnetic sensors, load sensors, chemical sensors, biological sensors, and/or temperature sensors; processors or other circuits; electrical motors; actuators; and the like. In one embodiment, the implanted electrical device 118 is embodied as an anisotropic magneto resistive sensor (AMR sensor). In one particular embodiment, the implanted electrical device 118 is embodied as an HMC1023 3-axis Magnetic Sensor commercially available from Honeywell International, Incorporated of Morristown, N.J. It should be appreciated that the implanted electrical device 118 receives power only while the primary coil 12, 26, 48 is energized via the power signal to produce the alternating magnetic field and the secondary coil 16 is exposed to the alternating magnetic field such that a current is induced in the secondary coil 16.

In some embodiments, the implantable orthopaedic device 14 may also include a transmitter 120. The transmitter 120 is coupled in communication with the implanted electrical device 118 via a number of interconnects 122 and receives power from the secondary coil 16 in a manner similar to the device 118. The transmitter 120 is configured to transmit data received from the implanted electrical device 118 to the receiver 104 of the power circuit 22 via a wireless communication link 124. For example, in embodiments wherein the implanted electrical device 118 is a pressure sensor, the transmitter 120 is configured to transmit pressure data received from the device 118 to the receiver 104. In response, the control circuit may be configured to display the pressure data to the caregiver on the display 102. The transmitter 120 may transmit the data to the receiver 104 using any suitable wireless communication protocol such as, for example, Bluetooth, wireless USB, Wi-Fi, WiMax, Zigbee, or the like.

The implantable orthopaedic device 14 may also include an energy storage device 126. The energy storage device 126 may be embodied as any device capable of storing an amount of energy for later use by the implanted electrical device 118. For example, the energy storage device 126 may be embodied as a rechargeable battery such as a nickel cadmium battery or a storage capacitor and associated circuitry. Regardless, the energy storage device 126 is configured to be charged (i.e., energy is stored in the device 126) while the orthopaedic device 14 is being powered by the cooperation of the power circuit 22, the primary 12, 26, 46, and the secondary coil 16. Once the device 14 is no longer receiving power from the secondary coil 16, the energy storage device 126 begins providing power to the implanted electrical device 118. Once the energy storage device 126 becomes drained of energy, the device 126 may be recharged via the power circuit 22 and the primary coil 12, 26, 46. In this way, the device 118 may be powered over long periods of time.

Figure 12:
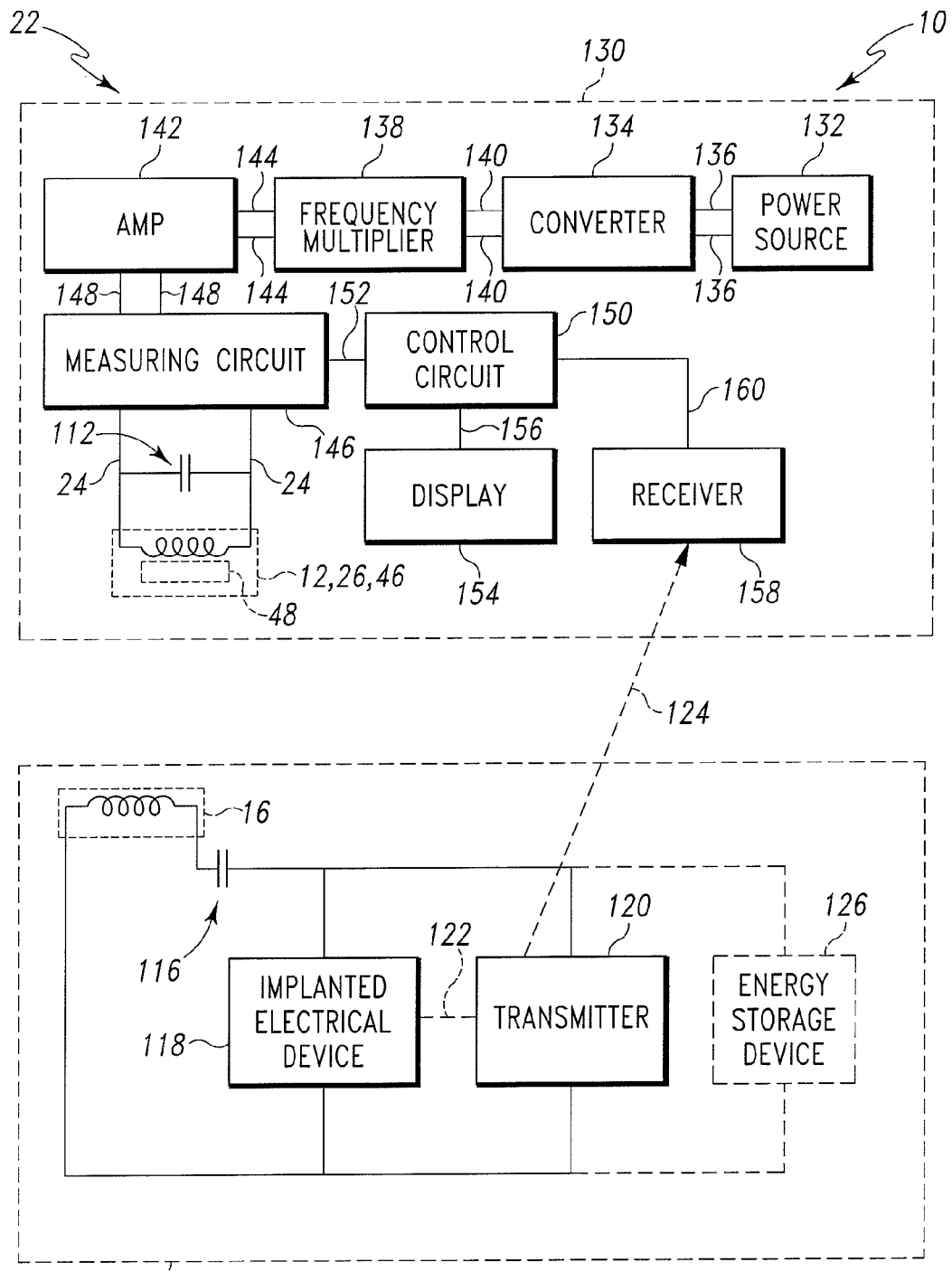
FIG. 12 is a block diagram of another embodiment of a transcutaneous energy transfer system.

Referring now to FIG. 12, in one embodiment, the power circuit 22 and primary coil 12, 26, 46 are positioned in a portable housing 130. In some embodiments, the portable housing 130 is embodied as a hand-held housing, which facilitates the positioning of the power circuit 22 and primary coil 12, 26, 46 by the caregiver. In such embodiments the caregiver may quickly reposition the primary coil 12, 26, 46, move or sweep the primary coil 12, 26, 46 over a portion of the patient 20 and transport the power circuit 22 and the primary coil 12, 26, 46 to a new location. To further facilitate portability, in such embodiments, the power circuit 22 includes a direct current (DC) power source 132, such as rechargeable or replaceable batteries. Accordingly, the housing 130 may be moved about the patient 20 without the need of an AC cord or AC power outlet.

The power circuit 22 also includes a converter 134 coupled with the power source 132 via a number of interconnects 136. The converter 134 is configured to convert the DC power signal received from the DC power source 132 to an AC power signal. The converter 134 may be embodied as any circuit or device capable of converting the DC power signal to a AC power signal including, for example, discrete circuitry, integrated circuitry, or a combination thereof. A frequency multiplier 138 is coupled with the converter 134 via a number of interconnects 140. The frequency multiplier 138 is configured to convert the AC power signal received from the converter 134 to an AC power signal having a predetermined frequency. That is, the frequency multiplier 138 produces an AC power signal having a frequency that matches the resonant frequency of the primary coil 12, 26, 46. The frequency multiplier 138 may be embodied as any circuit or device capable of multiplying the frequency of the AC power signal by a predetermined amount.

The power circuit 22 also includes an amplifier 142 coupled with the frequency multiplier 138 via a number of interconnects 144. The amplifier 142 is configured to amplify the output signal received from the frequency multiplier 138 and produce an amplified output signal having a predetermined amplitude. The predetermined amplitude of the amplified output signal may be determined based on the particular primary coil 12, 26, 46 used and the application of the system 10. The amplifier 142 may be embodied as any type of amplifier capable of amplifying the output signal of the frequency multiplier 138 to the predetermined amplitude. For example, the amplifier 142 may be formed from discrete and/or integrated circuitry.

A measuring circuit 146 is coupled with the amplifier 142 via a number of interconnects 148 and to the primary coil 12, 26, 46 via the interconnects 24. The measuring circuit 146 is configured to measure the amount of power supplied to the primary coil 12, 26, 46. In some embodiments, the meter 94 is coupled in parallel with the outputs of the amplifier 144 (i.e., the amplifier 142 is coupled directly to the primary coil 12, 26, 46 and to the measuring circuit 146). In other embodiments, the measuring circuit 146 may have a pass-through input-output configuration. Regardless, the measuring circuit 146 has a large input impedance such that the effects of the measuring circuit 146 on the amplified power signal are reduced. The measuring circuit 146 may be any type of measuring circuit capable of measuring the power supplied to the primary coil 12, 26, 46. For example, the measuring circuit 146 may be formed from discrete and/or integrated circuitry.

A control circuit 150 is communicatively coupled with the measuring circuit 146 via a number of interconnects 152, with a display 154 via a number of interconnects 156, and with a receiver 158 via a number of interconnects 160. The control circuit 150 may be similar to the control circuit 100 described above in regard to FIG. 11. The control circuit 150 may be embodied as any type of control circuit capable of performing the functions described herein including, but not limited to, discrete circuitry and/or integrated circuitry such as a processor, microcontroller, or an application specific integrated circuit (ASIC). The receiver 158 is configured to wirelessly receive data from the implantable orthopaedic device 14 and transmit the data to the control circuit 150. The control circuit 150 may display the data, or computed data based thereon, on the display 154. Additionally, the control circuit 150 may display power usage data received from the measuring circuit 146 on the display 154. The display 154 may be embodied as any type of display capable displaying data to the caregiver including, for example, a segmented light emitting diode (LED) display, a liquid crystal display (LCD), or the like.

In addition to the power circuit 22, the primary coil 12, 26, 46 (and the core 48 in some embodiments) and the tuning capacitor 112 are positioned in the portable housing 130. As discussed above in regard to FIG. 11, the tuning capacitor 112 is used to configure the resonant frequency of the primary coil 12, 26, 46 and, in some embodiments, is selected such that the quality factor (Q) of the resulting resonance curve is high. The tuning capacitor 112 may be physically coupled to a portion (e.g., bobbin 32) of the primary coil 12, 26, 46 or may be separate from the primary coil 12, 26, 46. Regardless, the tuning capacitor 112 is coupled in parallel with the primary coil 12, 26, 46 to form a parallel resonance circuit.

Although illustrated and described above as separate components, it should be appreciated that any two or more of the power source 132, the converter 134, the frequency multiplier 138, the amplifier 142, the measuring circuit 146, the control circuit 150, the display 154, and the receiver 158 may be included as a single component capable of performing the functions of the individual components. For example, in some embodiments, the converter 134 and the frequency multiplier 138 may be embodied as a single circuit, integrated or discrete, that is capable of converting the DC power signal from the power source 132 to an AC power signal having a frequency that matches the resonant frequency of the associated primary coil 12, 26, 46. As such, the interconnects 136, 140, 144, 148, 152, 156, 160 may be embodied as any type of interconnects capable of providing electrical connection between the various components of the power circuit 22 such as, for example, wires, cables, PCB traces, internal integrated circuit connections, or the like.

Figure 13:
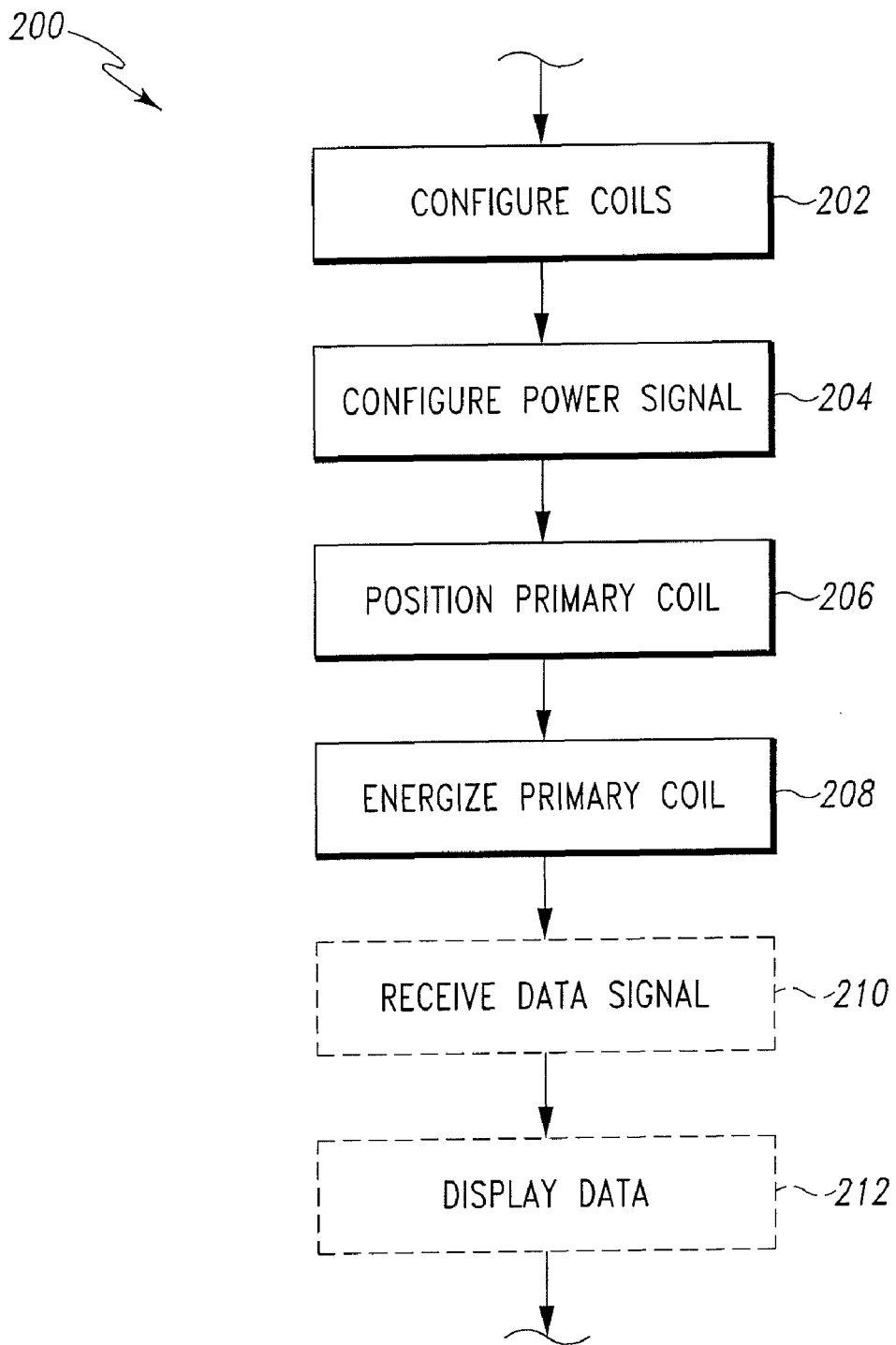
FIG. 13 is a simplified flow chart of an algorithm for transcutaneously transferring an amount of energy.

Referring now to FIG. 13, an algorithm 200 for transcutaneously transferring an amount of energy to the implantable orthopaedic device 14 begins with a process step 202. In step 202, the resonant frequency of the primary coil 12, 26, 46 is configured to match the resonant frequency of the secondary coil 16 in the implantable device 14. For example, the tuning capacitor 112 may be selected or replaced such that the resulting resonant frequency of the primary coil 12, 26, 46 matches the resonant frequency of the secondary coil 16. In embodiments, wherein the tuning capacitor 112 is embodied as a variable capacitor, the capacitance of the tuning capacitor 112 may be adjusted to match the frequencies of the primary coil 12, 26, 46 and the secondary coil 16. As discussed above in regard to FIGS. 11 and 12, the turning capacitor 112 may be selected such that the quality factor (Q) of the resulting resonance curve is high. That is, the resonant frequency of the primary coil 12, 26, 46 matches a narrower bandwidth of frequencies.

In some embodiments, the resonant frequency of the secondary coil 16 of the implantable orthopaedic device 14 is predetermined based on the type of orthopaedic device 14. For example, all knee implants may be configured to a resonant frequency of about 5 kilohertz while all hip implants may be configured to a resonant frequency of about 4 kilohertz. In such embodiments, the resonant frequency of the secondary coil 16 may already be configured to the predetermined frequency. In addition, in embodiments wherein the orthopaedic device 14 has been previously implanted in the patient 20, the resonant frequency of the secondary coil is also predetermined (i.e., pre-configured prior to the surgical procedure). However, in other embodiments or applications, such as when the orthopaedic device 14 has not yet been implanted into the patient 20, the resonant frequency of the secondary coil 16 may be configured. To do so, as discussed above in regard to FIG. 11, the capacitance value of the tuning capacitor 116 is selected such that the resulting resonant frequency of the secondary coil 16 matches a predetermined frequency (e.g., 5 kilohertz). Additionally, the turning capacitor 116 may be selected such that the quality factor (Q) of the resulting resonance curve is low. That is, the resonant frequency of the secondary coil 16 matches a broad bandwidth of frequencies.

Once the resonant frequency of the primary coil 12, 26, 46 (and, in some embodiments, the secondary coil 16) has been configured, the algorithm 200 advances to process step 204. In process step 204, the power signal is configured. That is, the frequency of the power signal is configured to match the resonant frequency of the primary coil 12, 26, 46. To do so, the waveform generator 90 or the frequency multiplier 138 may be configured to produce an output signal having a frequency that matches the resonant frequency of the primary coil 12, 26, 46. For example, if the resonant frequency of the primary coil 12, 26, 46 is configured to 6 kilohertz, the waveform generator or the frequency multiplier 138 is configured to produce an output signal having a frequency of about 6 kilohertz.

Once the resonant frequency of the power signal has been matched to the resonant frequency of the primary coil 12, 26, 46, the primary coil 12, 26, 46 is positioned in process step 206. To do so, in embodiments including the primary coil 26, the portion of the patient 20 (e.g., leg 18) wherein the implantable orthopaedic device 14 is located is positioned in the aperture 28 such that the primary coil 26 circumferentially surrounds the portion of the patient 20. The primary coil 26 is then positioned such that the primary coil 26 is substantially coplanar with the implanted orthopaedic device 14. Because the aperture 28 has a diameter 30 greater than the width of the portion of the patient 20, the primary coil 26 may be positioned such that coil 26 is spaced away from the skin of the patient 20 to reduce the likelihood of damaging the skin of the patient 20. To position the primary coil 26 in the desired location, the caregiver may grasp the bobbin 32 or handle 38 to move the coil 26.

Alternatively, in embodiments including the primary coil 46, the primary coil 46 may be positioned near the portion of the patient 20 (e.g., leg 18) wherein the implantable orthopaedic device 14 is located. The primary coil 46 is positioned such that the primary coil 46 is substantially coplanar with the orthopaedic device 14. The primary coil 46 may also be spaced away from the skin of the patient 20 to reduce the likelihood of damaging the skin of the patient 20. To position the primary coil 46 in the desired location, the caregiver may grasp the sleeve 56 or a portion of the core 48 to move the coil 46.

In embodiments wherein the power circuit 22 and the primary coil 12, 26, 46 are positioned in a portable housing 130, the caregiver may position the primary coil 12, 26, 46 may positioning the portable housing 130 such that the housing 130 (i.e., the primary coil 12, 26, 46 located within the housing 130) is near and substantially coplanar with the implantable orthopaedic device 14. To do so, the caregiver may grasp the housing 130, or a handle coupled therewith, to move the housing 130 and the primary coil 12, 26, 46 to the desired location.

Once the primary coil 12, 26, 46 has been positioned at the desired location, the primary coil 12, 26, 46 is energized via a power signal from the power circuit 22 in process step 208. In response, the primary coil 12, 26, 46 generates an alternating magnetic field. The alternating magnetic field is received by the secondary coil 16 (i.e., the secondary coil 16 is exposed to the magnetic field) and the primary coil 12, 26, 46 and the secondary coil 16 become inductively coupled. Because the secondary coil 16 is exposed to an alternating magnetic field, a current is induced in the secondary coil 16. In this way, the secondary coil 16 provides power to the implanted electrical device(s) and other circuitry of the implantable orthopaedic device 14. Because the resonant frequencies of the power signal, the primary coil 12, 26, 46, and the secondary coil 16 are matched; the transfer efficiency of energy from the primary coil 12, 26, 46 to the secondary coil 16 is increased. In embodiments including the display 102 or display 154, the power supplied to the primary coil 12, 26, 46 may be displayed to the caregiver.

Additionally, in some embodiments, the algorithm 200 may include a process step 210 in which data is received from the implantable orthopaedic device 14. The received data may be any type of data obtained by or produced by the implanted electrical device 118. For example, in embodiments wherein the implanted electrical device 118 is embodied as a sensor, sensory data may be received by the receiver 104 from the transmitter 120 of the orthopaedic device 14. In some embodiments, the implanted electrical device 118 is configured to measure or determine the data while receiving power from the secondary coil 16. In other embodiments, such as in embodiments including the energy storage device 126, the implanted electrical device 118 may be configured to continually or periodically measure or determine the data. Regardless, the data so determined is transmitted to the power circuit 22 via the wireless link 124.

Once the data is received by the power circuit 22 (via the receiver 104, 158), the data may be displayed to the caregiver via the associated display 102, 154 in process step 212. To do so, the control circuit 100, 150 may control the display 102, 154 to display the data. In addition, the control circuit 100, 150 may be configured to process the data to determine additional data based on the data received from the orthopaedic device 14.

Figure 14:
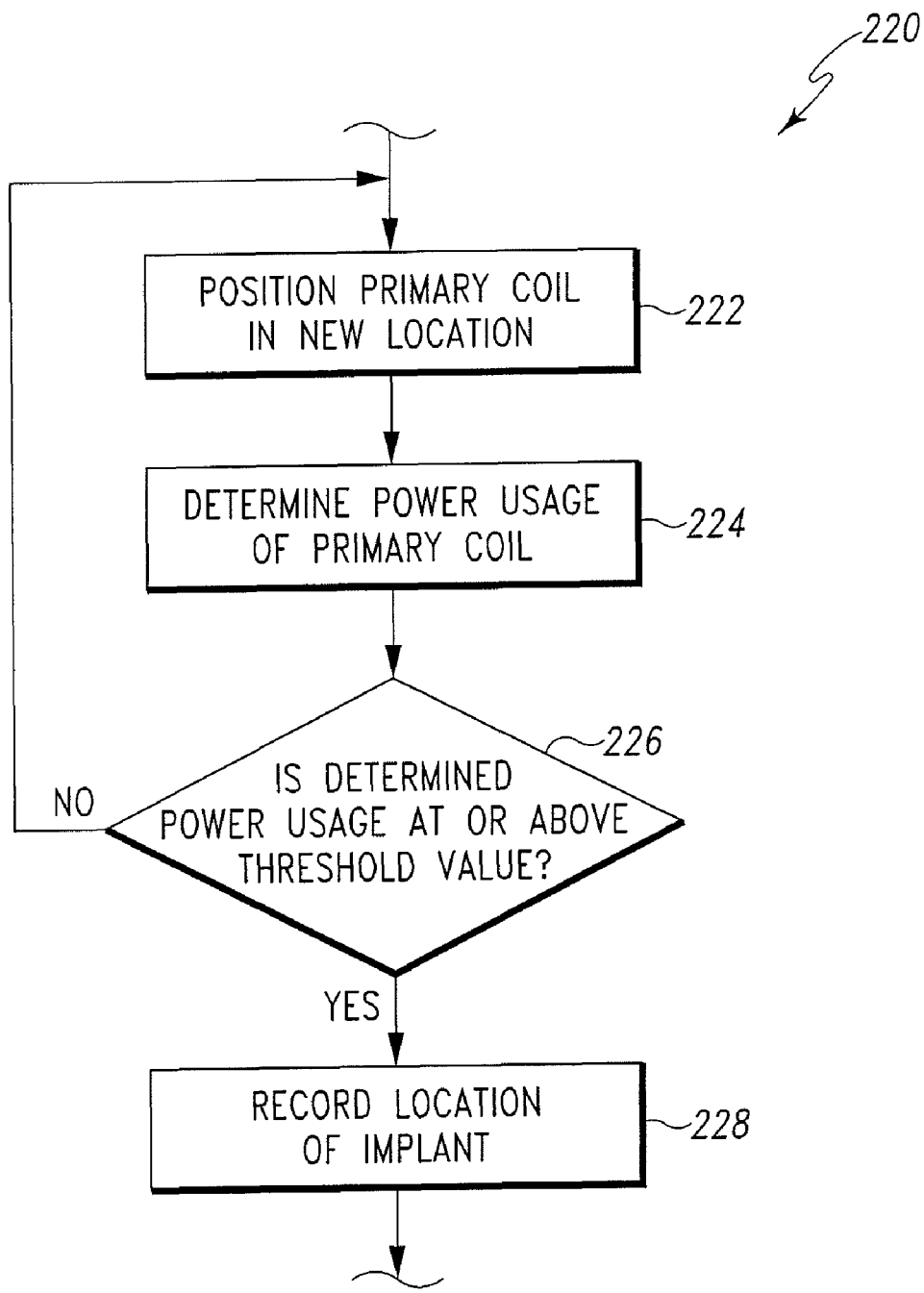
FIG. 14 is a simplified flow chart of an algorithm for determining a location of an implanted orthopaedic device in the body of a patient.

Referring now to FIG. 14, an algorithm 220 for determining a location of an orthopaedic device implanted in a patient's body begins with a process step 222. In the process step 222, the primary coil 12, 26, 46 is positioned in a new location. That is, in the first iteration of the algorithm 220, the primary coil 12, 26, 46 is positioned in an initial location near the portion of the patient 20 wherein the orthopaedic device 14 is implanted. To do so, in embodiments including the primary coil 26, the portion of the patient 20 (e.g., leg 18) wherein the implanted orthopaedic device 14 is located is positioned in the aperture 28 such that the primary coil 26 circumferentially surrounds the portion of the patient 20. Alternatively, in embodiments including the primary coil 46, the primary coil 46 is positioned near the portion of the patient 20 (e.g., leg 18) wherein the orthopaedic device 14 is implanted. Because the exact location of the orthopaedic device 14 may not be known, the primary coil 12, 26, 46 may not be substantially coplanar with the orthopaedic device 14 during the first iteration of the algorithm 220 (i.e., while the primary coil 12, 26, 46 is at the initial location).

Once the primary coil 12, 26, 46 is positioned in the initial location in step 222, the power usage of the primary coil 12, 26, 46 is determined in process step 224. To do so, the meter 94 or measuring circuit 146 determines the power supplied to the primary coil 12, 26, 46. In some embodiments, the power supplied to the primary coil 12, 26, 46 may also be displayed to the caregiver via the display 102, 154. The power usage of the primary coil 12, 26, 46 varies according to the inductive coupling of the primary coil 12, 26, 46 and the secondary coil 16. That is, as the secondary coil 16 draws power from the alternating magnetic field, the primary coil 12, 26, 46 uses an increased amount of power to maintain the alternating magnetic field. Accordingly, the power usage of the primary coil 12, 26, 46 increases as the primary coil 12, 26, 46 becomes more coplanar, and more inductively coupled, with the secondary coil 16.

In process step 226, the algorithm 220 determines if the power usage at the present location of the primary coil 12, 26, 46 is at or above a predetermined threshold value (e.g., a user defined maximum value). To do so, the control circuit 100, 150 may be configured to store previously measured power usage amounts in a memory device. The power usage of the primary coil 12, 26, 46 at the present location may then be compared to the stored power usage amounts. If the power usage of the primary coil 12, 26, 46 at the present location is not at or above the predetermined threshold value, the algorithm 220 loops back to the process step 222 in which the primary coil 12, 26, 46 is positioned in a new location. It should be appreciated that the process steps 222, 224, 226 may be repeated until a location is found at which the power supplied to the primary coil 12, 26, 46 is at or above the predetermined threshold. For example, a caregiver may move or sweep the primary coil 12, 26, 46 over the location of the patient 20 wherein the orthopaedic device 14 is implanted. As the caregiver sweeps the primary coil 12, 26, 46 over the patient 20, the power usage of the primary coil 12, 26, 46 varies. A location at which the power supplied to the primary coil 12, 26, 46 is at or above the predetermined threshold value may be determined by monitoring the display 102, 104. Alternatively, in some embodiments, the power circuit 22 may include an audible or visual indicator that is activated when the primary coil 12, 26, 46 sweeps over a location at which the power supplied to the primary coil 12, 26, 46 is at or above a predetermined threshold value.

The location(s) at which the power usage of primary coil 12, 26, 46 is at or above the predetermined threshold value correlates to a location at which the primary coil 12, 26, 46 is substantially coplanar with the secondary coil 16 of the implanted orthopaedic device 14. Accordingly, once such a location is found, the location of the implanted orthopaedic device 14 is recorded in process step 228. The location of the device 14 may be recorded by, for example, establishing a mark on the skin of the patient 20, recording coordinate data identifying the location of the device 14, or the like.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A limb brace comprising:
   a brace structure configured to be coupled to a limb of a patient;
   a primary coil coupled to the brace structure and having a resonant frequency; and
   means for matching the resonant frequency of the primary coil to a resonant frequency of a secondary coil spaced apart from the brace structure and coupled to an implantable orthopaedic device.

2. The limb brace of claim 1, wherein the primary coil is configured to circumferentially surround a portion of the limb of the patient while the brace structure is coupled to the limb.

3. The limb brace of claim 1, wherein the primary coil is a toroidal primary coil.

4. The limb brace of claim 1, wherein the primary coil is wound around a portion of a "C"-shaped ferrite core.

5. The limb brace of claim 1, wherein the primary coil is configured to be inductively couplable with the secondary coil while the brace structure is coupled to the limb of the patient.

6. The limb brace of claim 1, wherein the primary coil is configured to be spaced away from a skin surface of the limb while the brace structure is coupled to the limb of the patient.

7. The limb brace of claim 1, wherein the resonant frequency of the primary coil is adjustable to match the resonant frequency of a different secondary coil of an implantable orthopaedic device.

8. The limb brace of claim 1, wherein the resonant frequency of the primary coil is less than about 9 kilohertz.

9. The limb brace of claim 8, wherein the resonant frequency of the primary coil is about 5 kilohertz.

10. The limb brace of claim 1, wherein the brace structure is configured to couple to a leg of the patient.

11. An apparatus, comprising:
    a brace structure configured to be coupled to a limb of a patient;
    a primary coil coupled to the brace structure;
    an implantable orthopaedic device;
    a secondary coil coupled to the implantable orthopaedic device; and
    wherein the primary coil has a resonant frequency matched to a resonant frequency of the secondary coil.

12. The apparatus of claim 11, wherein the primary coil is configured to circumferentially surround a portion of the limb of the patient while the brace structure is coupled to the limb.

13. The apparatus of claim 11, wherein the primary coil is a toroidal primary coil.

14. The apparatus of claim 11, wherein the primary coil is wound around a portion of a "C"-shaped ferrite core.

15. The apparatus of claim 11, wherein the primary coil is configured to be inductively couplable with the secondary coil while the brace structure is coupled to the limb of the patient.

16. The apparatus of claim 11, wherein the primary coil is configured to be spaced away from a skin surface of the limb while the brace structure is coupled to the limb of the patient.

17. The apparatus of claim 11, wherein the resonant frequency of the primary coil is adjustable to match the resonant frequency of a different secondary coil coupled to the implantable orthopaedic device.

18. The apparatus of claim 11, wherein the resonant frequency of the primary coil is less than about 9 kilohertz.

19. The apparatus of claim 18, wherein the resonant frequency of the primary coil is about 5 kilohertz.

20. The apparatus claim 11, wherein the brace structure is configured to couple to a leg of the patient.

* * * * *